United States Patent [19]
Pryor et al.

[11] Patent Number: 5,337,992
[45] Date of Patent: Aug. 16, 1994

[54] SUPPORT DEVICE FOR AMBULATORY PATIENT

[75] Inventors: John W. Pryor, Oceanside; Jeffery W. Pryor, Vista, both of Calif.

[73] Assignee: Pryor Products, Inc., Oceanside, Calif.

[21] Appl. No.: 14,859

[22] Filed: Feb. 8, 1993

[51] Int. Cl.⁵ .............................................. A47E 29/00
[52] U.S. Cl. ................... 248/125; 5/507.1; 5/558; 5/662; 248/219.2
[58] Field of Search .............. 248/121, 125, 128, 176, 248/219.2, 207; 5/507.1, 662, 658, 503.1

[56] References Cited

U.S. PATENT DOCUMENTS

| | | | |
|---|---|---|---|
| 3,400,829 | 9/1968 | Youngson | 5/507.1 X |
| 4,332,378 | 6/1982 | Pryor | 482/68 |
| 4,489,454 | 12/1984 | Thompson | 5/503.1 |
| 4,691,397 | 9/1987 | Netzer | 5/507.1 |
| 4,725,027 | 2/1988 | Bekanich | 248/125 |
| 4,744,536 | 5/1988 | Bancalari | 248/125 |
| 4,945,592 | 8/1990 | Sims et al. | 5/508 |
| 5,094,418 | 3/1992 | McBarnes, Jr. et al. | 248/125 X |
| 5,149,036 | 9/1992 | Sheehan | 248/215 |
| 5,236,162 | 8/1993 | Desjardins | 248/214 |

OTHER PUBLICATIONS

LifeCare Equipment Transport Systems brochure, Abbott Laboratories, May 15, 1991, pp. 1, 2, 3 and 6.

Primary Examiner—Ramon O. Ramirez
Attorney, Agent, or Firm—Brown, Martin, Haller & McClain

[57] ABSTRACT

A support for an ambulatory patient has a hub member with a mounting device for mounting the hub member on a vertical IV pole of a wheeled IV stand. An arcuate hand grip member is secured to the hub member and radially spaced from the mounting device for gripping by an ambulatory patient receiving medication from an IV bottle on the stand. A downwardly facing, U-shaped channel is provided on the hub member for allowing the support to be hooked onto the rim of the head or foot board of a bed or gurney.

17 Claims, 3 Drawing Sheets

SUPPORT DEVICE FOR AMBULATORY PATIENT

BACKGROUND OF THE INVENTION

This invention relates generally to support devices for ambulatory patients, and is particularly concerned with a support or hand grip device for mounting on an IV stand.

In U.S. Pat. No. 4,332,378 of John W. Pryor, an ambulatory patient support stand is described in which a hand grip is secured to a vertical IV pole with a wheeled base. The hand grip comprises a toroidal or circular grip element secured to a central hub by radial spokes, the hub having an opening for mounting over the IV pole. The grip is secured at an appropriate height for grasping easily by an ambulatory patient, allowing the patient to move around relatively freely while hooked up to medication suspended from IV hangers at the top of the IV pole. This avoids the problems of existing walkers which do not allow IV stands to be easily moved along with the patient without risk of upsetting the stand or tripping the patient. The hand grip secured to the wheeled IV stand itself combines the advantages of a mobile walker with an integral IV stand, so that only one unit must be wheeled around.

SUMMARY OF THE INVENTION

It is an object of the present invention to provide a new and improved support device for ambulatory patients.

According to the present invention, a patient support device is provided which comprises a hub member having an opening for fitting the hub member over a vertical post of a wheeled IV stand, an elongate, arcuate hand grip member secured to the hub member and radially spaced from the opening, and a mounting device for releasably supporting the hub member on the head or foot board of a hospital bed or gurney.

Preferably, the mounting device comprises a downwardly facing, straight channel or groove on the undersurface of the hub member for hooking over the top of a head or foot board. This allows the support device to be used with an IV stand alone by an ambulatory patient, or alternatively allows the IV stand to be secured to the head or foot board of a bed or gurney while the patient is in bed or lying on the gurney. In the latter case, the hand grip can be grasped by medical personnel in order to wheel the bed and IV stand together as a unit while moving the patient from one location to another.

In a preferred embodiment of the invention, the hub member has a flat upper surface for supporting other equipment and items to be transported with the patient, with a cut-out or recess having radially extending side edges extending from the opening up to opposite ends of the hand grip. The hub member has a straight forward edge facing away from the hand grip, and the channel for hooking onto a head or foot board extends parallel to and adjacent the forward edge of the device on the undersurface of the hub member.

The periphery of the mounting device is therefore part circular, and the opening for fitting over an IV pole is not centrally positioned but is closer to the straight, forward edge of the device, so that the majority of the mounting device projects in one direction only from the IV stand. This takes up less space and allows the device to be hooked onto a head or foot board without projecting over the bed itself where it would obstruct the patient.

The support device of this invention can be easily mounted on a wheeled IV stand to allow a patient to move around easily and securely while hooked up to instruments and medications supported on the IV stand. The hand grip allows medical staff and patients to push the stand safely and easily. The support device also allows an attached stand to be secured to a hospital bed or gurney while stationary or for transportation with the bed or gurney.

BRIEF DESCRIPTION OF THE DRAWINGS

The present invention will be better understood from the following detailed description of a preferred embodiment of the invention, taken in conjunction with the accompanying drawings, in which like reference numerals refer to like parts, and in which.

DESCRIPTION OF THE PREFERRED EMBODIMENT

Figure 5:
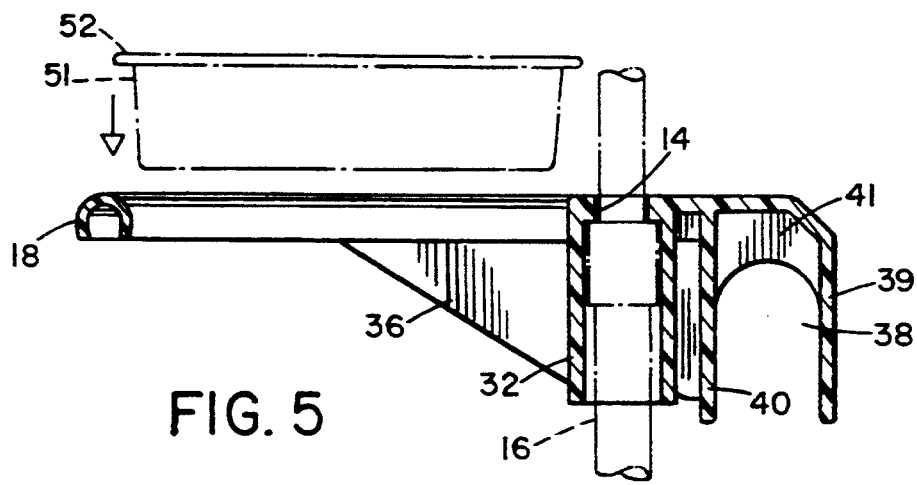
FIG. 5 is a sectional view taken on line 5—5 of FIG. 2.

A support device 10 according to a preferred embodiment of the present invention is illustrated in the drawings. As best illustrated in FIGS. 1 and 5, the device 10 basically comprises a hub member 12 having an opening 14 for fitting the hub member over the vertical post 16 of a wheeled IV stand, and an elongate, arcuate hand grip member 18 radially spaced from the opening 14 and secured at opposite ends to the hub member 12.

Hub member 12 has a generally flat upper surface 20 with a cut-out 24 having radial side edges 26, 27 extending from opening 14 up to the opposite ends of hand grip member 18. The hub member has a straight, forward peripheral edge 28 and spaced parallel sides 30, 31 extending rearwardly from the forward edge 28 up to the grip member 18. Opening 14 is positioned centrally between sides 30 and 31 and adjacent forward edge 28, so that the support member takes up a minimum of space in a forward direction when secured on an IV post, reducing the risk of a user bumping into objects or other people when pushing the IV stand from the rear while grasping grip member 18.

Figure 3:
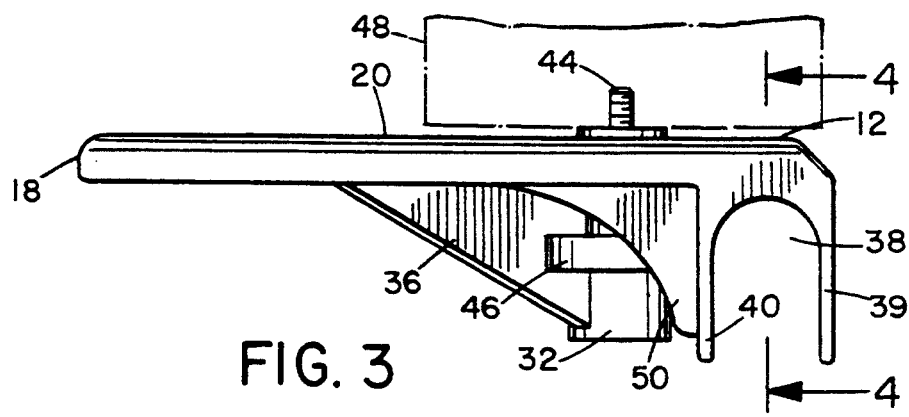
FIG. 3 is a side elevation view of the unit.

A tubular hub 32 projects downwardly from the undersurface of the hub member surrounding opening 14 to provide support against wobbling of the device when mounted on an IV stand. Radial webs or spines 36 project outwardly from hub 32 along radial edges 26, 27 for additional structural support. A U-shaped, downwardly facing channel 38 is formed in the undersurface of the device between spaced side walls 39, 40. Channel 38 is adjacent to forward edge 28, as best illustrated in FIGS. 1, 3 and 5. The channel 38 is open-ended and extends between the opposite sides 30, 31 of the hub member. Spaced, arch-shaped webs 41 are provided along the length of the channel. Channel 38 is designed to be hooked over the upper edge 42 of a head or foot board 43 of a hospital bed or gurney, as illustrated in dotted outline in FIG. 6. The width of the channel is sufficient to allow it to fit over the widest dimension head boards used in hospitals and other medical facilities.

Figure 1:
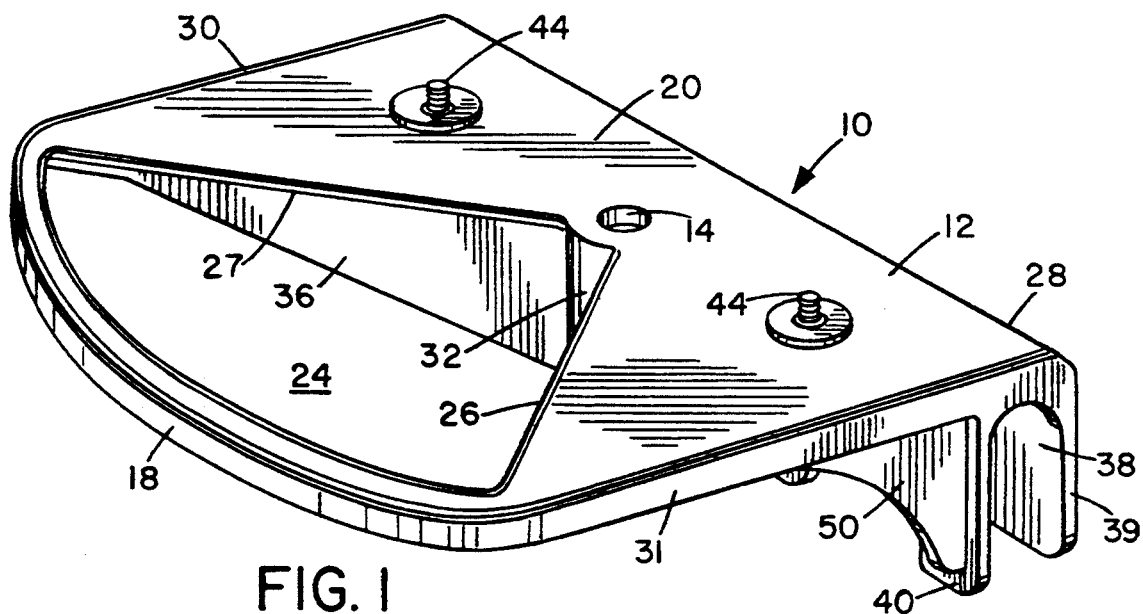
FIG. 1 is a perspective view of the support device according to a preferred embodiment of the invention.
Figure 4:
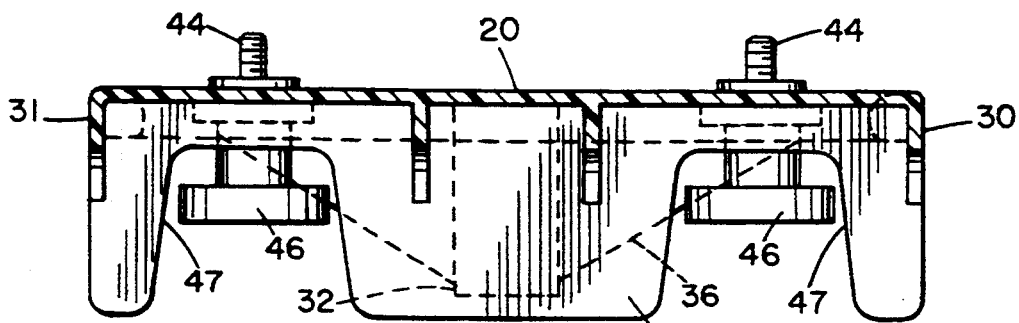
FIG. 4 is a sectional view taken on line 4—4 of FIG. 3.

A pair of spring-loaded mounting screws 44 project upwardly from the undersurface of the device through openings in the flat upper surface of the hub member on opposite sides of the opening 14, as best illustrated in FIGS. 1 and 4. The screws 44 are each spring-loaded out of tubular housing 45 into the extended position illustrated in the drawings. Each housing has an enlarged head or knob 46 located under the flat surface, and cut-outs or recesses 47 are provided in side wall 40 of the channel 38 for access to the screw heads, as illustrated in FIG. 4. The screws 44 can be used to secure equipment 48 such as IV pumps or the like which are placed on the flat upper surface of the hub member, as illustrated in dotted outline in FIG. 3. The housing of such equipment will often have screw holes on its undersurface, and can therefore easily be secured to support device 10 simply by locating the end of one of the screws 44 in the screw hole, and screwing it into engagement with the screw hole via head 46. If equipment having no screw holes is used, it can simply be placed on the flat upper surface of the device, in which case the spring-loaded, projecting end of the screw 44 will be pushed out of the way into housing 45. The equipment can be secured to the IV pole in this case, for example. Optionally, the spring-loaded mechanism 44 may be eliminated in an alternative embodiment in which equipment is simply placed on hub member 12 or secured to the IV pole.

Figure 2:
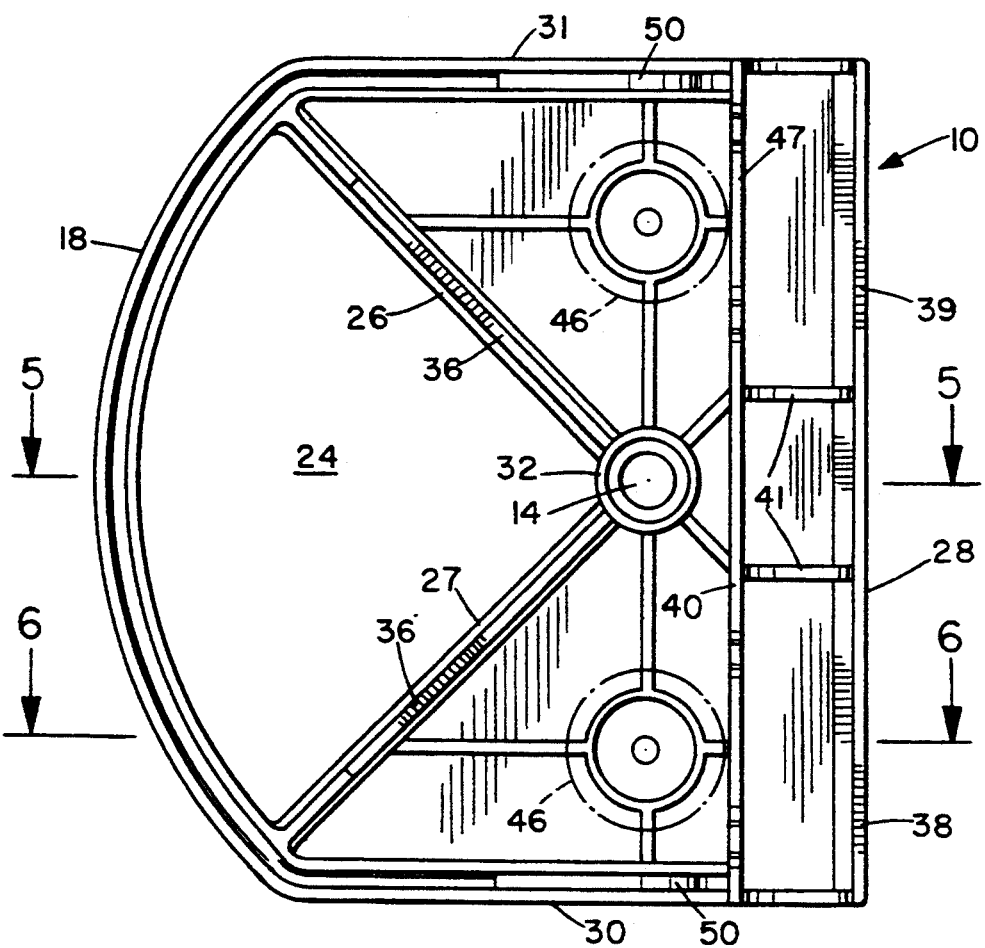
FIG. 2 is a bottom plan view of the unit.

Additional strengthening webs 50 are provided on the undersurface of the hub member extending from the opposite ends of channel side wall 40 along the sides 30, 31 of the hub member, as best illustrated in FIGS. 1 and 2.

Figure 7:
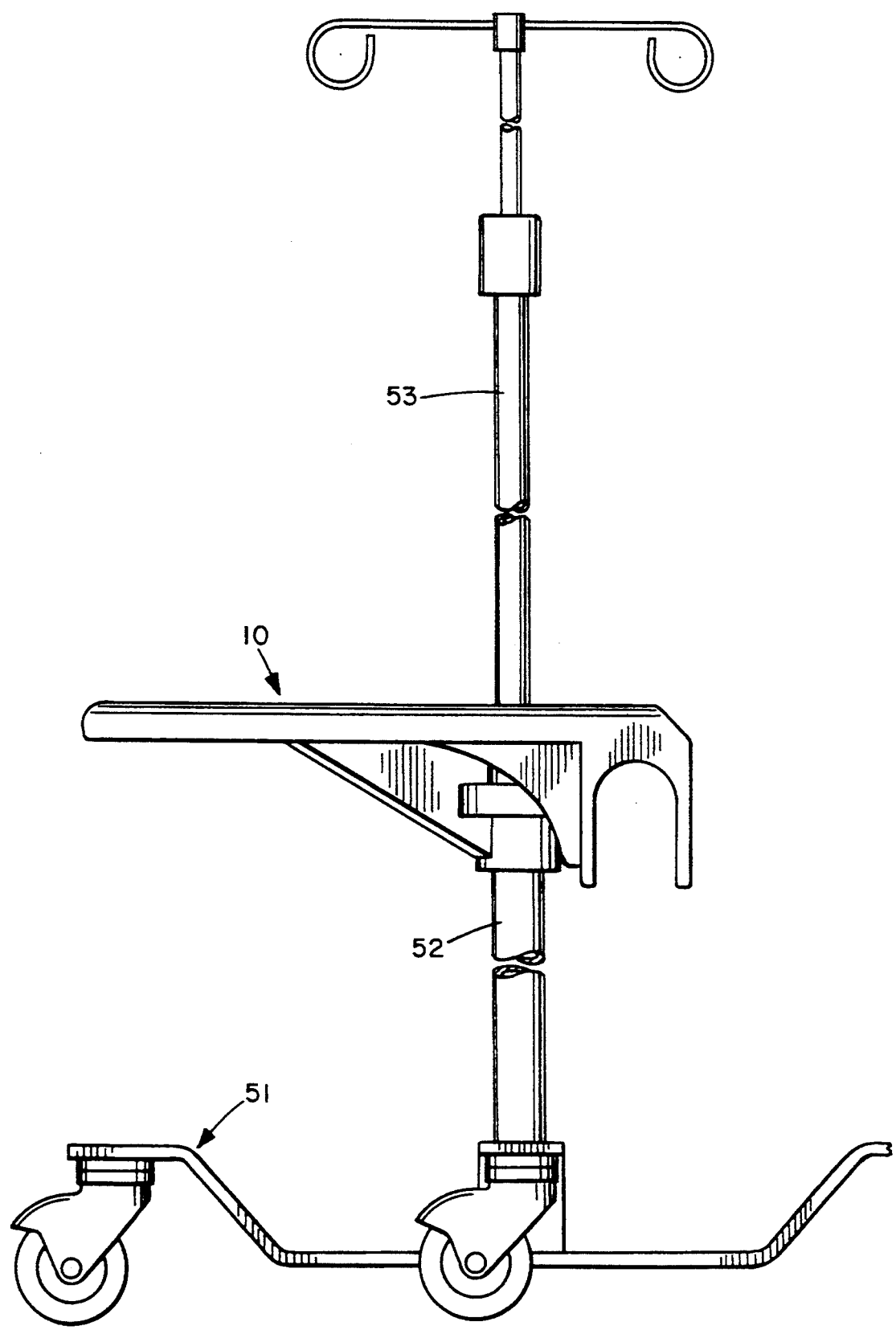
FIG. 7 is a side elevation view illustrating the support device attached to a wheeled IV stand.

As illustrated in FIGS. 5 and 7, the hub member is mounted on an IV stand having a wheeled base 51 at the intersection between two telescopically interengaged portions 52, 53 of the IV pole, in a similar manner to the push grip described in U.S. Pat. No. 4,332,378 referred to above, the contents of which are incorporated herein by reference. The hub member is first placed over the upper end of the larger diameter, lower portion 52 of the IV pole or stand, and the mating upper portion 53 of the pole is then inserted into the lower portion. This supports the hub member securely with hand grip 18 at an appropriate height for gripping and pushing of the hand grip member by patients or medical personnel.

The generally sector-shaped cut-out in the flat upper surface of the stand can be used to support a utility tray 51 of similar shape, as illustrated in dotted outline in FIG. 5. The rim 52 of the tray will be seated on the periphery of the cut-out, and the tray can then be used to carry various items with the stand.

Figure 6:
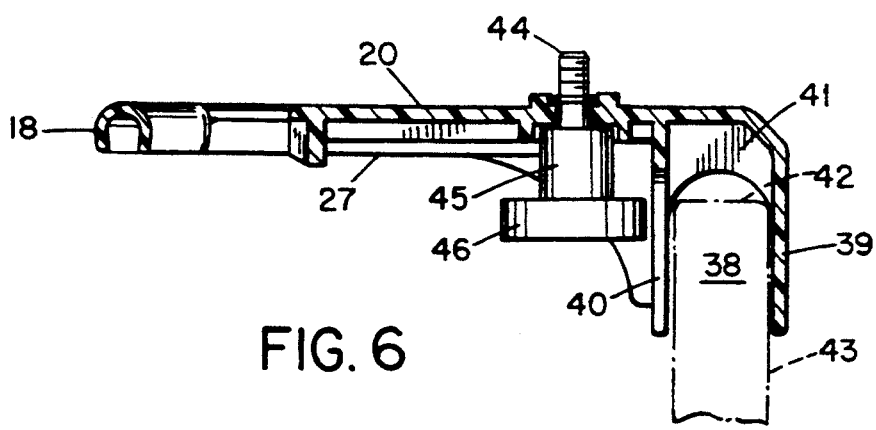
FIG. 6 is a sectional view taken on line 6—6 of FIG. 2.

The support device 10 is preferably molded of a light weight plastic material such as glass-fiber impregnated nylon which is strong and durable but light in weight. The hand grip member 18 is of generally U-shaped or channel cross-section, as illustrated in FIGS. 5 and 6, with the arcuate upwardly facing portion of the hand grip being of a suitable diameter for comfortable grasping by a wide range of different individuals. Preferably, the diameter of the hand grip element is around 1.9 centimeters.

The width of the hub member between the opposite sides 30, 31 is preferably around 13 inches, while the spacing between the opening 14 and the straight forward edge 28 of the hub member is preferably of the order of 3 to 4 inches. Thus, the forward portion of the hub member will not project a significant distance outwardly from the IV pole so that it does not take up a large amount of space and also will be less likely to be pushed into other objects or people when the stand is pushed by a patient or medical technician. The radial spacing between the hub opening and the handgrip is preferably of the order of 8 to 9 inches.

The support with integral hand grip 18 is convenient and easy to use, and takes up a minimal amount of space. It can be hooked onto a head or foot board at its forward edge via channel 38 to provide a support table as well as a gripping handle for pushing the bed or gurney. When mounted on an IV pole, it also acts to secure the IV pole to the bed so that it can be used to supply medication to a patient in the bed both while the bed is stationary and when it is moved around. The support 10 and attached IV pole are simply lifted up to the appropriate height for hooking channel 38 over the rim of head or foot board 43.

Although a preferred embodiment of the invention has been described above by way of example only, it will be understood by those skilled in the field that modifications may be made to the disclosed embodiment without departing from the scope of the invention, which is defined by the appended claims.

I claim:

1. A patient support for an IV stand, comprising:
   a hub member having mounting means for mounting the hub member on a vertical IV pole extending transversely through said hub member, at a location spaced between the opposite ends of the IV pole;
   an elongate, arcuate hand grip member secured to the hub member and radially spaced from the mounting means at a first, radial spacing; and
   a supporting device on the hub member for releasably supporting the hub member on the head or foot board of a hospital bed or gurney.

2. The support as claimed in claim 1, wherein the supporting device comprises a downwardly facing, U-shaped channel on the hub member for releasably hooking over the top of a head or foot board.

3. The support as claimed in claim 1, wherein the hub member has a flat upper surface for supporting equipment.

4. The support as claimed in claim 3, wherein the flat upper surface has a recess with radially extending side edges extending outwardly from said mounting means, and the hand grip is secured at opposite ends to the outer ends of said radially extending side edges.

5. The support as claimed in claim 3, wherein said flat upper surface includes securing means for releasably securing equipment onto said surface.

6. The support as claimed in claim 1, wherein said hub member has a straight, forward peripheral edge and said supporting device extends along said forward edge.

7. The support as claimed in claim 6, wherein said supporting device comprises a downwardly facing, U-shaped channel which is open at its opposite ends.

8. The support as claimed in claim 1, wherein said hub member has a downwardly projecting tubular hub for fitting over an IV pole, the tubular hub comprising said mounting means, the hub member having a forward edge facing away from said hand grip member, and the hub member and said forward edge being spaced apart by a second spacing which is less than the first radial spacing between said hub member and said hand grip member.

9. The support as claimed in claim 1, wherein the mounting means has a mounting axis and the hand grip member extends in a direction transverse to said mounting axis, whereby said hand grip member is oriented horizontally when the hub member is mounted on a vertical IV pole.

10. A support device for an ambulatory patient, comprising:
   a hub member having an opening for mounting the hub member on a vertical IV pole extending transversely through the opening, the opening comprising means for seating over an IV pole to support said hub member on said IV pole;
   an elongate, arcuate hand grip member secured to the hub member and radially spaced at a first radial spacing from the opening;
   the hub member having a forward edge facing away from the hand grip member and spaced from said opening by a second spacing; and
   the second spacing between the forward edge of the hub member and the opening being substantially less than the radial spacing between the hand grip member and the opening.

11. The support device as claimed in claim 10, wherein the hub member has a downwardly facing, U-shaped channel extending along said forward edge for hooking over the rim of a head or foot board of a bed or gurney.

12. The support device as claimed in claim 11, wherein the U-shaped channel has parallel inner and outer side walls, and the opening is positioned adjacent the inner side wall of the channel.

13. The support device as claimed in claim 10, wherein the hub member has a rearwardly facing, V-shaped cut-out having radial side edges projecting outwardly from said opening, and said hand grip member is secured at opposite ends to the opposite, outer ends of the radial side edges of said cut-out.

14. The support device as claimed in claim 13, wherein said V-shaped recess and hand grip member together comprise means for selectively supporting a sector-shaped utility tray.

15. The support device as claimed in claim 10, wherein said hub member has a flat upper surface for supporting equipment, and mounting devices on said upper surface on opposite sides of said opening for selectively securing equipment onto said surface.

16. The support device as claimed in claim 15, wherein said mounting devices each comprise a housing mounted below the flat upper surface of said hub member, a screw member projecting upwardly out of said housing, said hub member having openings aligned with each of said screw members, and biasing means urging said screw member upwardly through said opening into an operative position.

17. An ambulatory patient support stand, comprising:
   a wheeled base;
   a vertical IV pole projecting upwardly from the base, the pole having an upper end and a lower end;
   a hub member mounted on the IV pole at a position intermediate the ends of the pole;
   an elongate, arcuate hand grip member secured to the hub member and radially spaced from the pole;
   the hand grip member being vertically spaced from the base at a predetermined height for gripping by a person in an erect position; and
   a supporting device on the hub member for releasably supporting the hub member on the head or foot board of a hospital bed or gurney.

* * * * *